US007084128B2

(12) United States Patent
Yerxa et al.

(10) Patent No.: US 7,084,128 B2
(45) Date of Patent: Aug. 1, 2006

(54) METHOD FOR REDUCING INTRAOCULAR PRESSURE

(75) Inventors: Benjamin R. Yerxa, Raleigh, NC (US); Robert Plourde, Jr., Chapel Hill, NC (US); Edward G. Brown, Cary, NC (US); Ward M. Peterson, Morrisville, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 337 days.

(21) Appl. No.: 10/347,255

(22) Filed: Jan. 15, 2003

(65) Prior Publication Data

US 2003/0186928 A1 Oct. 2, 2003

Related U.S. Application Data

(60) Provisional application No. 60/350,742, filed on Jan. 18, 2002.

(51) Int. Cl.
*A61K 31/70* (2006.01)
*C07H 21/00* (2006.01)

(52) U.S. Cl. .............................. 514/48; 514/46; 514/47; 514/49; 514/50; 514/51; 514/912; 514/913; 514/762; 514/763; 536/25.6; 536/26.1

(58) Field of Classification Search .................. 514/46, 514/47, 48, 49, 50, 51, 912, 913, 762, 763, 514/256, 299, 42, 43, 44; 536/25.6, 26.1
See application file for complete search history.

(56) References Cited

U.S. PATENT DOCUMENTS 5,219,849 A 6/1993 Lotti et al. ................. 514/214
5,545,626 A 8/1996 Stein et al. ................. 514/44
5,900,407 A 5/1999 Yerxa et al. ................. 514/47
6,319,908 B1 11/2001 Yerxa et al. ................. 514/51

FOREIGN PATENT DOCUMENTS

| WO | WO 98/34942 | 8/1998 |
| WO | WO 99/61012 | 12/1999 |
| WO | WO 00/03741 | * 1/2000 |
| WO | WO 81/87913 | 11/2001 |
| WO | WO 02/09702 | 2/2002 |
| WO | WO 02/16381 | 2/2002 |

OTHER PUBLICATIONS

Peral et al., Investigat. Opthalmol. Vis. Science, vol. 41, S255 (2000).*
European Search Report, Jun. 2003.
Crawford, et al., "Agonist–induced $Ca^{2+}$ mobilization in cultured bovine and human corneal endothelial cells," *Current Eye Res.*, 12(4):303–311 (1993).

(Continued)

*Primary Examiner*—James O. Wilson
*Assistant Examiner*—Howard V. Owens, Jr.
(74) *Attorney, Agent, or Firm*—Howrey LLP; Viola T. Kung

(57) ABSTRACT

The present invention is directed to a method of reducing intraocular pressure. The method comprises administering to a subject a pharmaceutical composition comprising an effective amount of a purinerginic receptor ligand, which is a mononucleoside polyphosphate or dinucleoside polyphosphate defined by general Formula I. The method of the present invention is useful in the treatment or prevention of ocular hypertension, such as glaucoma, including primary and secondary glaucoma. The method can be used alone to reduce intraocular pressure. The method can also be used in conjunction with other therapeutic agents or adjunctive therapy commonly used to treat glaucoma to enhance the therapeutic effect of reducing the intraocular pressure.

27 Claims, 1 Drawing Sheet

OTHER PUBLICATIONS

Jensen, et al., "ATP Release from the Cornea Following Mild Mechanical Stimulation," poster presentation at American Academy of Optometry annual meeting, Dec. 1999, Seattle, WA.

Jumblatt, et al., "Regulation of Ocular Mucin Secretion by $P2Y_2$ Mucleotide Receptors in Rabbit and Human Conjuinctiva," *Exp. Eye Res.* 67(3): 341–6 (1998).

Lee, et al., "Alterations of Intracellular Calcium in Human Non–pigmented Ciliary Epithelial Cells of the eye," *Exp. Eye. Res.*, 48: 733–743 (1989).

Mitchell, et al., "A release mechanism for stored ATP in ocular ciliary epithelial cells," *Proc. Natl. Acad. Sci. U.S.A.*, 95: 7174–7178 (1998).

Peral, et al., "Effects of diadenosine polyphosphates on introcular pressure and pupil size in New Zealand rabbits", *Investig. Opthalmol. Vis. Science*, 41:S255 (2000).

Pintor, et al., "Effect of ATP and adenine nucleotides on intraocular pressure in New Zealnad rabbits," *Investig. Opthalmol. Vis. Science*, 41:S255 (2000).

Shahidullah, et al., "Mobilisation of intracellular calcium by $P2Y_2$ recepors in cultured, non–transformed bovine ciliary eptithelial cells," *Curr. Eye Res.*, 16(10): 1006–1016 (1997).

Taylor, *The Pharmacological Basis of Therapeutics*, Editors: A.G. Gilman, L.S. Goodman, T.W. Rall, and F. Murad, Macmillan Publishing Co., New York, 7: 123–125 (1985).

Wax and Coca–Prados, "Receptor–Mediated Phosphoinositide Hydrolysis in Human Ocular Ciliary Epithelial Cells," *Investig. Opthalmol. Vis. Science*, 30(7): 1675–1679 (1989).

Wax, et al., "Purinergic Receptors in Ocular Ciliary Eithelial Cells," *Exp. Eye Res.* 57: 89–95 (1993).

* cited by examiner

METHOD FOR REDUCING INTRAOCULAR PRESSURE

This application claims the benefit of U.S. Provisional Application No. 60/350,742, filed Jan. 18, 2002.

TECHNICAL FIELD

This invention relates to a method of lowering intraocular pressure and thereby treating ocular hypertension and/or glaucoma.

BACKGROUND OF THE INVENTION

Glaucoma is a slowly progressive blinding disease usually associated with chronic elevation of intraocular pressure (IOP). Sufficiently high and persistent intraocular pressure is believed to result in damage to the optic disc at the juncture of the optic nerve and retina, resulting in degeneration of retinal ganglion cells and blindness characteristic of glaucoma. However, the mechanism whereby IOP elevation (also known as ocular hypertension) leads to glaucoma is not well understood. Additionally, a fraction of patients with typical visual field loss associated with glaucoma do not show abnormal elevated IOP levels (known as low-tension or normal-tension glaucoma).

Glaucoma is primarily classified as open-angle, closed-angle, or congenital, and further classified as primary and secondary. Glaucoma is treated with a variety of pharmacological and surgical approaches. In cases where glaucoma is associated with ocular hypertension, pharmacological treatment comprises adrenergic agonists (epinephrine, dipevefrin, apraclonidine), cholinergic agonists (pilocarpine), beta blockers (betaxolol, levobunolol, timolol), carbonic anhydrase inhibitors (acetozolamide) or more recently, prostaglandin analogues (latanoprost, Lumigan™) and alpha adrenergic agonists (brimonidine). These pharmacological approaches help restore the IOP to a normotensive state either by inhibiting the production of aqueous humor by the ciliary body, or facilitating aqueous humor outflow across the trabecular meshwork. The congenital form of glaucoma rarely responds to therapy and is more commonly treated with surgery. In narrow angle glaucoma, the aqueous outflow is enhanced by freeing of the entrance to the trabecular space at the canal of Schlemm from blockade by the iris, as a result of the drug-induced contraction of the sphincter muscle of the iris (Taylor, pp. 123–125, in *The Pharmacological Basis of Therapeutics*, 7$^{th}$ Ed, Eds., A. G. Gilman, L. S. Goodman, T. W. Rall, and F. Murad, MacMillan Publishing Company, New York, (1985)).

In wide-angle, or chronic simple, glaucoma, the entry to the trabeculae is not physically obstructed; the trabeculae, a meshwork of pores of small diameter, lose their patency. Contraction of the sphincter muscle of the iris and the ciliary muscle enhances tone and alignment of the trabecular network to improve resorption and outflow of aqueous humor through the network to the canal of Schlemm (Watson, *Br. J. Opthalmol.* 56: 145–318 (1972); Schwartz, *N. Engl. J Med.*, 290: 182–186 (1978); Kaufman, et al., *Handbook of Experimental Pharmacology* 69: 149–192 (1984)).

Acute congestive (narrow angle) glaucoma is nearly always a medical emergency in which the drugs are essential in controlling the acute attacks, but long-range management is usually based predominantly on surgery (peripheral or complete iridectomy). By contrast, chronic simple (wide-angle) glaucoma has a gradual, insidious onset and is not generally amenable to surgical improvement; and control of intraocular pressure depends upon permanent therapy.

Acute congestive glaucoma may be precipitated by the injudicious use of a mydriatic agent in patients over 40 years, or by a variety of factors that can cause pupillary dilatation or engorgement of intraocular vessels. Signs and symptoms include marked ocular inflammation, a semidilated pupil, severe pain, and nausea. The therapeutic objective is to reduce the intraocular pressure to the normal level for the duration of the attack. An anticholinesterase agent is instilled into the conjunctival sac with a parasympathomimetic agent for greatest effectiveness. A commonly used combination consists of a solution of physostigmine and salicylate, 0.5%, plus pilocarpine nitrate, 4%. Adjunctive therapy includes the intravenous administration of a carbonic anhydrase inhibitor such as acetozolamide to reduce the secretion of aqueous humor, or of an osmotic agent such as mannitol or glycerin to induce intraocular dehydration.

Therapy of chronic simple glaucoma and secondary glaucoma includes: (1) prostaglandin analogs (e.g. Xalatan®, Lumigan); (2) beta-adrenergic antagonists such as timolol maleate; (3) sympathomimetic agents (e.g. epinephrine, brimonidine); (4) cholinergic agents (e.g. pilocarpine nitrate, echothiophate iodide; and (5) carbonic anhydrase inhibitors (e.g. Dorzolamide®) (Dain Rauscher Wessels, *Glaucoma in the 21$^{st}$ Century: New Ideas, Novel Treatments* (2001)).

Latanaprost (Xalatan®) is a prostanoid agonist that is believed to reduce IOP by increasing the uveoscleral outflow of aqueous humor. Latanoprost is an isopropyl ester prodrug, and is hydrolyzed by esterases in the cornea to the biologically active acid. Xalatan® (0.005%) is prescribed for once-daily dosing and is shown to be equivalently effective as twice-daily dosing of 0.5% timolol. However, Xalatan® may gradually change eye color by increasing the amount of brown pigment in the iris. The long-term effect on the iris is unknown,. Eyelid skin darkening has also been reported in associated with the use of Xalatan®. In addition, Xalatan® may gradually increase the length, thickness, pigmentation, and number of eyelashes. Macular edema, including cystoid macular edema, has been reported during treatment with Xalatan®. These reports have mainly occurred in aphakic patients, in pseudophakic patients with a torn posterior lens capsule, or in patients with known risk factors for macular edema ((Ophthalmic PDR, 315–316 (2001)).

Beta-Adrenergic antagonists effectively lower IOP when administered twice daily as a topical solution. The mechanism of reduction is through inhibition of the production of aqueous humor formed by the ciliary body. Topical timolol causes fewer adverse effects than the anticholinesterase agents. However, it may induce hyperaemia of the conjunctiva, burning, stinging, and superficial punctate keratitis (Van Buskirk, *Ophthalmology* 87: 447–450 (1980)). It may also reduce tear flow, causing dry eye syndrome (Coakes, et. al., *Br. J. Ophthalmol* 65: 603–605 (1981)). A more serious side effect of beta-blockers is cardiac failure, thus this class of IOP-lowering agent is not indicated with cardiopulmonary disease.

Alpha-Adrenergic agonists, such as brimonidine and apraclonidine, control IOP by reducing the production of aqueous humor as well as enhancing uveoscleral outflow (Burke & Schwartz, *Survey of Ophthalmology* 41:S9–S18 (1996)). Topical ophthalmic solutions are absorbed systemically and can produce dry mouth, ocular hyperemia, headache, and foreign body sensation (Hoyng and van Beek, *Drugs* 59: 411–434 (2000)).

The use of long-acting anticholinesterase agents is associated with a greater risk of developing lenticular opacities and untoward autonomic effects. Treatment of glaucoma with potent, long-acting anticholinesterase agents (including demecarium, echothiophate, and isoflurophate) for 6 months or longer is associated with a high risk of developing cataracts (Axelsson, et al., *Acta Opthalmol. (Kbh.)* 44: 421–429 (1966); de Roetth, *J.A.M.A.* 195: 664–666 (1966); Shaffer, et al., *Am. J. Opthalmol.* 62: 613–618 (1966)).

Although development of cataracts is common in untreated comparable age groups, the incidence of lenticular opacities under such circumstances can reach 50%, with the risk increasing in proportion to the strength of the solution, frequency of instillation, duration of therapy, and age of patient (Laties, *Am. J. Opthalmol.* 68: 848–857 (1969); Kaufman, et al., pp. 149–192, in *Pharmacology of the Eye, Handbook of Experimental Pharmacology, Vol. 69*, Ed. M. L. Sears, Springer-Verlag, Berlin, (1984)).

Miscellaneous ocular side effects that may occur following instillation of anticholinesterase agents are headache, brow pain, blurred vision, phacodinesis, pericorneal injection, congestive iritis, various allergic reactions and, rarely, retinal detachment. When anticholinesterase drugs are instilled intraconjunctivally at frequent intervals, sufficient absorption may occur to produce various systemic effects that result from inhibition of anticholinesterase and butyryl-cholinesterase. Hence, cholinergic autonomic function may be enhanced, the duration of action of local anesthetics with an ester linkage prolonged, and succinylcholine-induced neuromuscular blockade enhanced and prolonged. Individuals with vagotonia and allergies are at particular risk.

Because the cholinergic agonists and cholinesterase inhibitors block accommodation, they induce transient blurring of far vision, usually after administration of relatively high doses over shorter duration. With long-term administration of the cholinergic agonists and anticholinesterase agents, the response diminishes due to a diminished number of acetylcholine receptors.

Long-acting anticholinesterase agents are not recommended when prostaglandin analogs, beta-adrenergic antagonists, sympathomimetic agonists, or other agents can control glaucoma.

Carbonic anhydrase inhibitors control IOP by inhibiting the formation of aqueous humor. Oral carbonic anhydrase inhibitors exhibit pronounced systemic side effects, but newer topical solutions have a better side effect profile. Frequent side effects associated with topical Dorzolamide® include burning and stinging, bitter taste, superficial punctate keratitis, and allergic reaction (Hoyng and van Beek, *Drugs* 59: 411–434 (2000)).

Other new agents have been assessed for treatment of glaucoma, including an $A_3$ subtype adenosine receptor antagonist, a calmodulin antagonist, and an antiestrogen (WO 00/03741); an oligonucleotide which may be substituted, or modified in its phosphate, sugar, or base so as to decrease intraocular pressure (U.S. Pat. No. 5,545,626); and a class of pyrazine, pyrimidine, and pyridazine derivatives, substituted by a non-aromatic azabicyclic ring system and optionally by up to two further substituents (U.S. Pat. No. 5,219,849).

Various studies have documented the presence of P2 purinergic receptors in the eye. Activation of $P2Y_2$ receptors in rabbit and human conjunctival cells was associated with an increase in mucin secretion (Jumblatt and Jumblatt, *Exp. Eye Res.* 67(3):341–6 (1998)). $P2Y_2$ receptor agonists, such as ATP, cause mucin secretion, and mechanical stimulus of the cornea triggers local ATP release (Jensen et al., poster presentation at American Academy of Optometry annual meeting, December, 1999, Seattle, Wash.). Studies of P2 purinergic receptors in ocular ciliary epithelial cells demonstrated a $P2_U$ purinergic receptor, that was preferentially coupled to UTP and associated with the stimulation of phosphoinositide hydrolysis in both bovine pigmented and human non-pigmented epithelial cells (Wax, et al., *Exp. Eye Res.* 57: 89–95 (1993)). ATP significantly increased formation of inositol phosphates in bovine corneal endothelial cells (Crawford, et al., *Current Eye Res.*, 12(4): 303–311 (1993) and in human ocular ciliary epithelial cells (Wax and Coca-Prados, *Investig. Opthalmol. Vis. Science*, 30 (7): 1675–1679 (1989)). Diadenosine tetraphosphate has been shown to lower intraocular pressure in rabbits (Peral, et.al., *Investig. Opthalmol. Vis. Science*, 41: S255 (2000). Alpha, Beta-Methylene adenosine triphosphate and beta, gamma methylene adenosine triphosphate also were shown to reduce intraocular pressure in rabbits (Pintor, et.al., *Investig. Opthalmol. Vis. Science*, 41: S255 (2000). Stimulation of $P2Y_2$ purinergic receptors in bovine ciliary epithelium was coupled to a pertussis toxin-sensitive G protein and associated with the activation of phospholipase C, leading to mobilization of calcium from intracellular stores (Shahidullah, et al., *Curr. Eye Res.*, 16(10): 1006–1016 (1997)). ATP was shown to cause a dose-dependent increase in intracellular calcium in the ciliary epithelial cells of the eye (Lee, et al., *Exp. Eye Res.*, 48: 733–743 (1989)). Mitchell, et al. (*Proc. Natl. Acad. Sci. U.S.A.*, 95: 7174–7178 (1998)) showed that both the bovine pigmented and non-pigmented ciliary epithelial cells store and release ATP and other purines that may effect aqueous humor outflow by paracrine and/or autocrine mechanisms.

As described above, agents commonly used to treat glaucoma may cause adverse side effects, such as eye pain, eye color darkening, headache, blurred vision or the development of cataracts. There exists a need for agents that are both safe and effective in the treatment of glaucoma. This invention provides a novel approach to reduce intraocular pressure and thereby treat glaucoma.

SUMMARY OF THE INVENTION

The present invention is directed to a method of reducing intraocular pressure. The method comprises administering to a subject a pharmaceutical composition comprising an effective amount of a purinergic receptor ligand of general Formula I. Optionally, the method comprises an additional step of measuring the intraocular pressure of the subject before and/or after administering the composition. The methods of the present invention are useful in the treatment or prevention of conditions associated with elevated intraocular pressure such as ocular hypertension or glaucoma.

The purinergic receptor ligands useful for this invention are mononucleoside or dinucleoside polyphosphates of general Formula I, or a pharmaceutically-acceptable salt thereof:

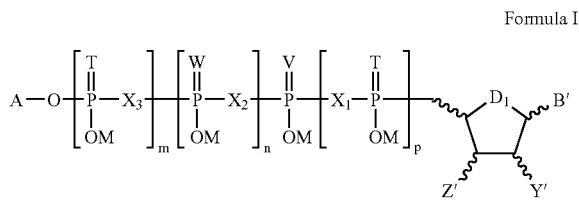

Formula I

The present method can be used alone to reduce the intraocular pressure. The method can also be used in conjunction with other therapeutic agents or adjunctive therapies commonly used to treat ocular hypertension or glaucoma to enhance the therapeutic effect of reducing the intraocular pressure.

DETAILED DESCRIPTION OF THE INVENTION

Figure 1:
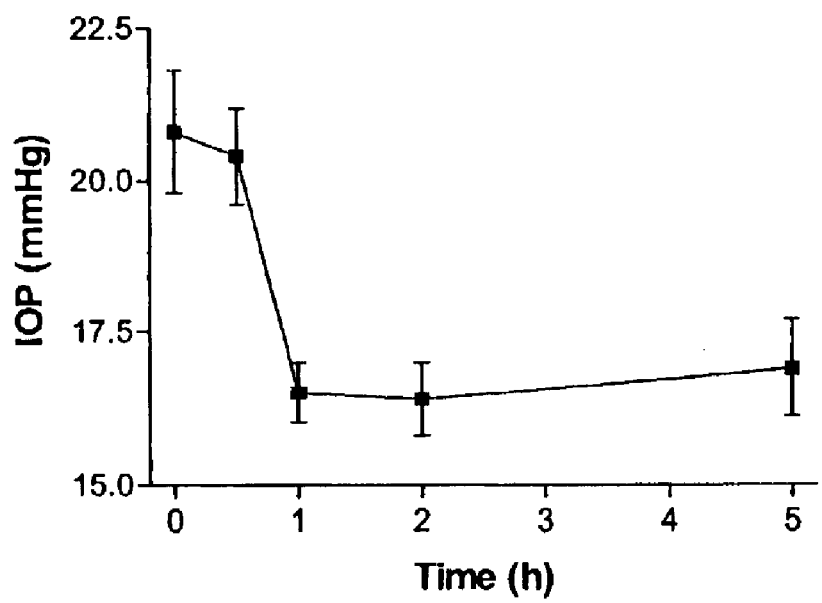
FIG. 1 shows the reduction of intraocular pressure in New Zealand white rabbits by 2'-(O)-3'-(O)-(benzyl) methylenedioxy-adenosine-5'-triphosphate.

The present invention provides a method of reducing intraocular pressure in a subject, thus treating disorders associated with elevated intraocular pressure. The method comprises administering to a subject a pharmaceutical composition comprising an effective amount of a purinergic receptor ligand. Optionally, the method comprises an additional step of measuring the intraocular pressure of the subject before and/or after administering the composition. The methods of the present invention are useful in the treatment or prevention of conditions associated with elevated intraocular pressure such as ocular hypertension or glaucoma. An effective amount of a purinergic receptor ligand is an amount that reacts with a purinergic receptor, leading to a reduction in intraocular pressure and/or amelioration of the symptoms of glaucoma.

The method of the present invention is useful for the management and/or treatment of primary glaucoma, which consists of two types: narrow angle or acute congestive and wide angle or chronic simple glaucoma. The method of the present invention is also useful for the management and/or treatment of secondary glaucoma.

Description of Compounds

The purinergic receptor ligands useful for this invention include compounds of Formula I, or a pharmaceutically-acceptable salt thereof:

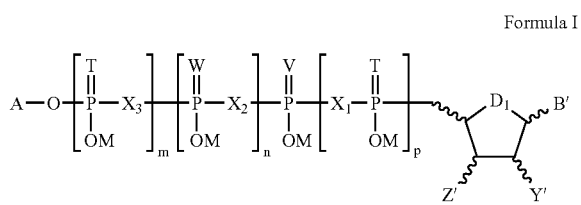

Formula I wherein:
$X_1$, $X_2$, and $X_3$ are independently oxygen, methylene, monochloromethylene, dichloromethylene, monofluoromethylene, difluoromethylene, or imido;
T, W, and V are independently oxygen or sulfur;
m=0, 1 or 2;
n=0 or 1;
p=0, 1, or 2;
where the sum of m+n+p is from 0 to 5;
each M is independently hydrogen or a pharmaceutically-acceptable inorganic or organic counterion;
A=M, or
A is a nucleoside residue which is defined as:

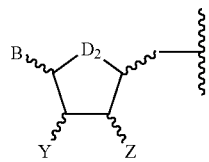

and is linked to the phosphate chain via the 5' position of the furanose or carbocycle;
Z is H, F or $OR_1$;
Z' is H, F or $OR_3$;
Y is H, F or $OR_2$;
Y' is H, F or $OR_4$;
$R_1$, $R_2$, $R_3$, and $R_4$ are independently H or a residue according to Formulas II and/or III;

provided that when A=M, at least one of Y', and Z' equals $OQ(R_5R_6R_7)$ under the definition of Formula II; or Y' and Z' taken together form a ring as defined in Formula III;
further provided that when A is a nucleoside, at least one of Y, Y', Z, or Z' equals $OQ(R_5R6R_7)$ under the definition of Formula II; or either Y and Z taken together, or Y' and Z' taken together form a ring as defined in Formula III;
$D_1$ and $D_2$ are independently O or C;

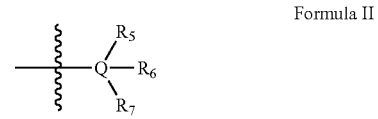

Formula II wherein:
Q is a carbon atom;
$R_5$, $R_6$, and $R_7$ are independently H, F, alkyl, cycloalkyl, aralkyl, aryl, substituted aralkyl, substituted aryl, or heterocyclic moiety, or
$R_5$ and $R_6$, are taken together to form a carbocyclic or heterocyclic ring of 4 to 7 members, such that the moiety defined according to Formula II when attached to the oxygen is an ether; or
$R_5$ and $R_6$ are taken together as oxygen or sulfur doubly bonded to Q, and $R_7$ is alkyl, cycloalkyl, aralkyl, substituted aralkyl, aryl, substituted aryl, or a heterocycle of 4 to 7 members, such that the moiety defined according to Formula II when attached to the oxygen is an ester or thioester; or
$R_5$ and $R_6$ are taken together as oxygen or sulfur doubly bonded to Q, and $R_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II when attached to the oxygen is a carbamate or thiocarbamate; or
$R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II when attached to the oxygen is a carbonate or thiocarbonate;

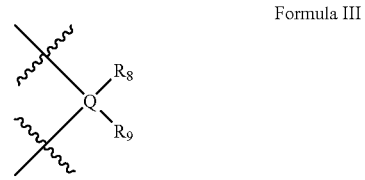

Formula III wherein $R_1$ and $R_2$ and/or $R_3$ and $R_4$ are taken together to form Q;
Q is a carbon atom;
$R_8$ and $R_9$ are taken together as oxygen or sulfur doubly bonded to Q to form a cyclical carbonate or thiocarbonate; or
$R_8$ is hydrogen, alkyl, cycloalkyl, aralkyl, aryl, substituted aralkyl, or substituted aryl, heterocycle or substituted heterocycle;
$R_9$ is hydrogen, alkyl, cycloalkyl, aralkyl, aryl, substituted aralkyl, or substituted aryl, heterocycle or substituted heterocycle, alkyloxy, cycloalkyloxy, aralkyloxy, aryloxy, substituted aralkyloxy, or substituted aryloxy, such that Q is part of an acetal-, ketal- or ortho ester moiety;

B and B' are independently a purine or a pyrimidine residue according to Formulas IV or V which is linked to the sugar via the 9- or 1-position, respectively;

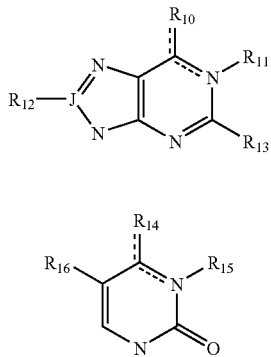

Formula IV

Formula V wherein:

$R_{10}$ and $R_{14}$ are independently hydroxy, oxo, amino, mercapto, alkylthio, alkyloxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or $R_{10}$ and $R_{14}$ are independently acylamino, according to Formula VI; or when $R_{10}$ or $R_{14}$ has as its first atom nitrogen, $R_{10}$ and $R_{11}$ or $R_{14}$ and $R_{15}$ are taken together to form a 5-membered fused imidazole ring (etheno compounds), optionally substituted on the imidazole ring of the etheno-compound with a substituted- or unsubstituted- alkyl, cycloalkyl, aralkyl, or aryl moiety, as described for $R_5$–$R_9$ above;

J is carbon or nitrogen, with the provision that when J is nitrogen, $R_{12}$ is not present;

$R_{11}$ is hydrogen, O (adenine 1-oxide derivatives) or is absent (adenine derivatives);

when present, $R_{12}$ is hydrogen, alkyl, azido, amino, alkylamino, arylamino or aralkylamino, hydroxy, alkoxy, aryloxy or aralkyloxy, sulfhydryl, alkylthio, arythio or aralkylthio, or $\omega$-X ($C_{1-6}$alkyl)G-, wherein X is substituted- or unsubstituted-amino, mercapto, hydroxy or carboxyl and G is chosen from —O-(to give an ether), —S-(to give a thioether), —$NR_{18}$-(to give an amine),—N(CO)$R_{18}$-(to give an amide), or N(CO)O$R_{18}$ (to give a carbamate);

$R_{13}$ is hydrogen, chlorine, fluorine, hydroxy, amino, mono-substituted amino, disubstituted amino, alkylthio, trifluoroalkylthio, arylthio, or aralkylthio, where the substituent on sulfur contains up to a maximum of 20 carbon atoms, with or without unsaturation;

$R_{15}$ is hydrogen, or acyl (e.g. acetyl, benzoyl, phenylacyl, with or without substituents);

$R_{16}$ is hydrogen, methyl, substituted- or unsubstituted-alkyl, halo, aryl, aralkyl, alkenyl, substituted alkenyl, alkynyl, or substituted alkynyl;

preferably at least one of B or B' is a purine; more preferably at least one of B or B' is an adenine;

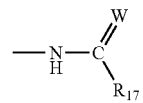

Formula VI wherein:

W is oxygen or sulfur;

$R_{17}$ is amino or mono- or disubstituted amino such that the moiety according to Formula VI is a urea or thiourea; or $R_{17}$ is alkoxy, aralkyloxy, aryloxy, substituted aralkyloxy, or substituted aryloxy, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide;

$R_{18}$ is alkyl, cycloalkyl, aralkyl, or aryl, with or without substituents or heteroatoms.

The furanosyl moieties independently can be in the D-configuration or in the L-configuration, with the D-configuration preferred. When $D_1$ and/or $D_2$ are oxygen, the furanose is preferably in the β-configuration and most preferably the furanose is in the β-D-configuration.

Preferred compounds of general Formula I are molecules whose structures fall within the definitions of Formula Ia:

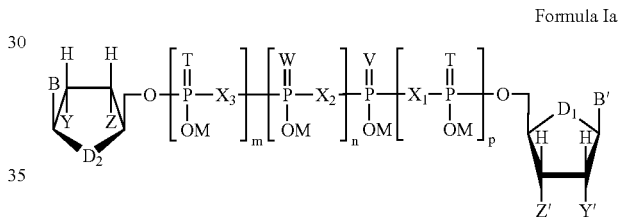

Formula Ia wherein:

M=H, or pharmaceutically-acceptable salt of this acid;

Z is H, or $OR_1$;

Z' is H, or $OR_3$;

Y is H, or $OR_2$;

Y' is H, or $OR_4$;

provided that at least one of Y, Y', Z, or Z' equals $OQ(R_5R_6R_7)$ under the definition of Formula II; or Y and Z taken together, and/or Y' and Z' taken together form a ring as defined in Formula III;

$D_1$=O;

$D_2$=O or C;

at least one of B or B' is an adenine residue according to Formula IV; and the sum of m+n+p is 3.

Preferred ether compounds of Formula Ia are those wherein D=O, B=B'=adenine, $R_1$, $R_2$, $R_3$ and $R_4$ are independently H or $CR_5R_6R_7$, wherein $R_5$=$R_6$=H, and $R_7$=alkyl or arylakyl, provided at least one of Y, Y', Z, and Z' equals to $OCR_5R_6R_7$. For examples, preferred compounds are selected from the group consisting of di-5'-[(2'-O-benzyl) adenosine]tetraphosphate, di-5'-[(3'-O-benzyl) adenosine] tetraphosphate, di-5'-[(2',3'-di-O-benzyl) adenosine]tetraphosphate, di-5'-[(2'-O-phenylethyl) adenosine]tetraphosphate, di-5'-[(3'-O-phenylethyl) adenosine]tetraphosphate, and di-5'-[(2',3'-di-O-phenylethyl) adenosine]tetraphosphate. Another set of preferred compounds are selected from the group consisting of P$^1$-5'-(2'-O-benzyl)adenosine-P$^4$-5''-adenosine tetraphosphate, P$^1$-5'-(3'-O-benzyl)adenosine-P$^4$-5''-adenosine tetraphosphate, P$^1$-5'-(2'-O-benzyl) adenosine-P$^4$-5''-(3''-O-benzyl)adenosine tetraphosphate, P$^1$-5'-(2'-O-phenylethyl)adenosine-P$^4$-5''-adenosine tetraphosphate, P$^1$-5'-(3'-O-phenylethyl)adenosine-P$^4$-5''-adenosine tetraphosphate, and P'-5'-(2'-O-phenylethyl)adenosine-P$^4$-5''-(3''-O-phenylethyl) adenosine tetraphosphate.

Preferred ester compounds of Formula Ia are those wherein D=O, B=B'=adenine, $R_1$, $R_2$, $R_3$, and $R_4$ are independently H or $CR_5R_6R_7$, $R_5$ and $R_6$ are taken together and $R_7$=alkyl or arylakyl, provided at least one of Y, Y', Z, and Z' equals to $OCR_5R 6R_7$. For examples, preferred compounds are selected from the group consisting of di-5'-[(2'-O-benzoyl) adenosine]tetraphosphate, di-5'-[(3'-O-benzoyl)adenosine]tetraphosphate, di-5'-[(2',3'-di-O-benzoyl)adenosine]tetraphosphate, di-5'-[(2'-O-phenylacetyl)adenosine]tetraphosphate, di-5'-[(3'-O-phenylacetyl)adenosine]tetraphosphate, and di-5'-[(2',3'-di-O-phenylacetyl)adenosine]tetraphosphate. Another set of preferred compounds are selected from the group consisting of P$^1$-5'-(2'-O-benzoyl)adenosine-P$^4$-5''-adenosine tetraphosphate, P$^1$-5'-(3'-O-benzoyl)adenosine-P$^4$-5''-adenosine tetraphosphate, P$^1$-5'-( 2'-O-benzoyl)adenosine-P$^4$-5''-(3''-O-benzoyl)adenosine tetraphosphate, P$^1$-5'-(2'—O—phenylacetyl)adenosine-P$^4$-5''-adenosine tetraphosphate, P$^1$-5'-(3'-O-phenylacetyl)adenosine-P$^4$-5''-adenosine tetraphosphate, and P$^1$-5'-(2'-O-phenylacetyl)adenosine-P$^4$-5''-(3''-O-phenylacetyl)adenosine tetraphosphate.

Other preferred compounds of Formula I are molecules whose structures fall within the definitions of Formula Ib:

Formula Ib

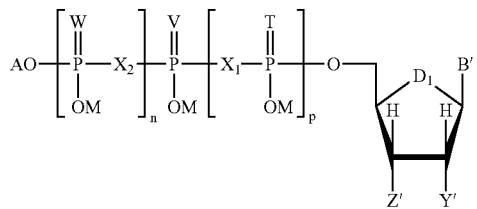

wherein:

A=M;

$X_1$ and $X_2$=O;

T, V, and W=O;

M=H or a pharmaceutically-acceptable salt of this acid;

Y' is H, or $OR_4$;

Z' is H, or $OR_3$;

with the provision that at least one of $R_3$ or $R_4$ is a residue according to Formula II;

or that Y' and Z' taken together form a ring as defined in Formula III;

$D_1$=O or C;

B is an adenine residue according to Formula IV; and the sum of n+p is 2.

Preferred ether compounds of Formula Ib are those wherein $D_1$=O, B'=adenine, $R_3$=$R_4$ =alkyl or arylakyl, provided at least one of Y' and Z' equals to $OR_3$ or $OR_4$. For example; preferred compounds are selected from the group consisting of 5'-(2'-O-benzyl)adenosine triphosphate, 5'-(3'-O-benzyl)adenosine triphosphate, 5'-(2',3'-di-O-benzyl)adenosine triphosphate, 5'-(2'-O-phenylethyl)adenosine triphosphate, 5'-(3'-O-phenylethyl)adenosine triphosphate, and 5'-(2',3'-di-O-phenylethyl)adenosine triphosphate.

Preferred ester compounds of Formula Ib are those wherein D=O, B=B'=adenine, $R_3$ and $R_4$ are independently H or $CR_5R_6R_7$, provided at least one of Y' and Z' equals to $OCR_5R_6R_7$, wherein $R_5$ and $R_6$ are taken together as oxygen, and $R_7$=alkyl or arylakyl. For example, preferred compounds are selected from the group consisting of 5'-(2'-O-benzoyl)adenosine triphosphate, 5'-(3'-O-benzoyl) adenosine triphosphate, 5'-(2',3'-di-O-benzoyl)adenosine triphosphate, 5'-(2'-O-phenylacetyl)adenosine triphosphate, 5'-(3'-O-phenylacetyl)adenosine triphosphate, and 5'-(2',3'-di-O-phenylacetyl)adenosine triphosphate.

Further preferred compounds of Formula I are molecules whose structures fall within the definitions of Formula Ic:

Formula Ic

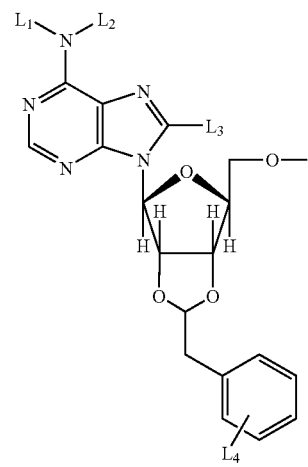 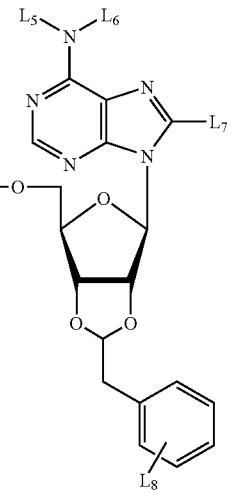

wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ and $L_8$ are independently selected from the group consisting of H, $C_1$–$C_6$ alkyl, aryl, $C_1$–$C_3$ alkylthio, $CF_3$, $CF_2CF_3$, —CN and —$N_3$.

A preferred compound of Formula Ic is that wherein $L_1=L_2=L_3=L_4=L_5=L_6=L_7=L_8=H$.

Further preferred compounds of Formula I are molecules whose structures fall within the definitions of Formula Id, or a 2'-ester or ether thereof, or 3'-ester or ether thereof:

Formula Id

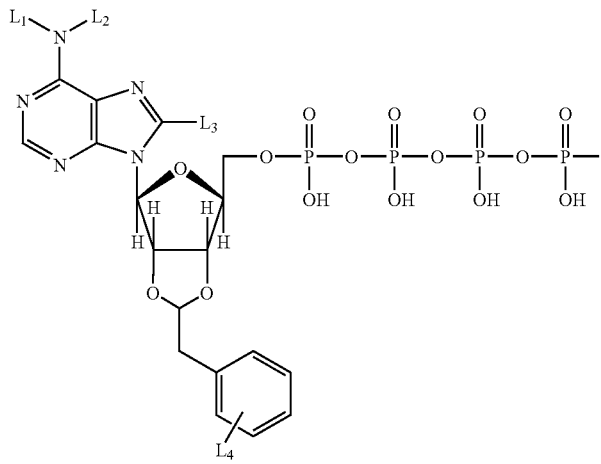

wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

A preferred compound of Formula Id is that wherein wherein $L_1=L_2=L_3=L_4=L_5=L_6=L_7=H$.

Further preferred compounds of Formula I are molecules whose structures fall within the definitions of Formula Ie:

Formula Ie

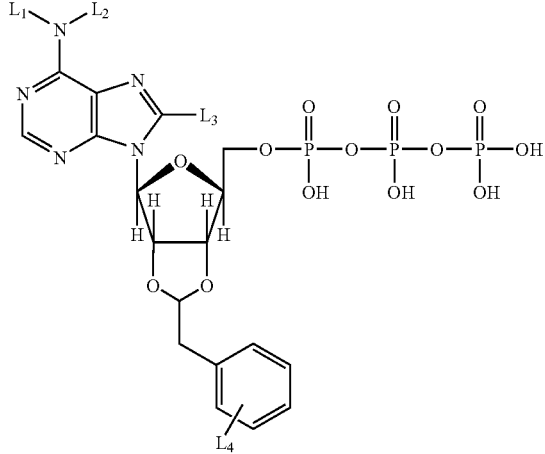

wherein $L_1$ and $L_2$ are independently selected from the group consisting of H, $C_1$–$C_4$ alkyl, phenyl, $C_1$–$C_{12}$ acyl and benzoyl;

$L_3$ is selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

A preferred compound of Formula Ie is that wherein $L_1=L_2=L_3=L_4=H$.

In general, alkyl groups include 1 to 8 carbons, either straight chained or branched, with or without unsaturation and with or without heteroatoms;

cycloalkyl groups include from 3 to 8 carbons, with or without unsaturation, and with or without heteroatoms;

aralkyl groups include from 1 to 5 carbons in the alkyl portion, and with monocyclic or polycyclic moieties from 4 to 8 carbons per ring, with or without heteroatoms in the aryl portion;

aryl groups include cyclic moieties from 4 to 10 carbons, with or without heteroatoms; and these groups may or may not bear substituents.

Preferred substituents on the foregoing groups can be, but are not limited to, hydroxy, nitro, methoxy, fluoro, chloro, bromo, iodo, methyl, ethyl, propyl, butyl, benzyl, thioalkyl, alkoxy, carboxyl, cyano, amino, substituted amino, trifluoromethyl, phenyl, cyclopropyl, cyclopentyl, and cyclohexyl.

Preferred heteroatoms are oxygen, nitrogen, and sulfur.

The present invention also encompasses non-toxic pharmaceutically acceptable salts of the above phosphate derivatives, such as, but not limited to, alkali metal salts such as lithium, sodium or potassium salts, or alkaline earth metal salts such as magnesium or calcium salts; or ammonium or mono-, di-, tri- or tetraalkyl ammonium salts, such as $NH_4^+$, $NEH_3^+$, $NE_2H_2^+$, $NE_3H^+$, or $NE_4^+$ (wherein E is $C_{1-4}$ alkyl) salts. Pharm acceptable salts are salts that retain the desired biological activity of the parent compound and do not impart undesired toxicological effects. Preferred counterions are monovalent ions such as sodium, lithium or potassium.

Methods of Preparing the Compounds

The compounds of the present invention can be conveniently synthesized by those skilled in the art using well-known chemical procedures. Mononucleoside mono-, di- and triphosphates, phosphonic acid derivatives and imidotriphosphates can be obtained from commercial sources or synthesized from the nucleoside using a variety of phosphorylation reactions found in the chemical literature. Symmetrical and unsymmetrical dinucleotide polyphosphates can be prepared by activation of a nucleoside mono-, di- or triphosphate with a coupling agent such as, but not limited to, dicyclohexylcarbodiimide or 1,1'-carbonyldiimidazole, followed by condensation with another nucleoside mono-, di-, or triphosphate, which can be the same as or different from the activated moiety. Activation of nucleoside triphosphates with dicyclohexylcarbodiimide gives a cyclical trimetaphosphate as the activated species, which can react with a variety of nucleophiles to install unique substituents on the terminal phosphate of a triphosphate.

The compounds of the present invention can be prepared by derivatization or substitution at the level of the nucleoside, followed by phosphorylation and condensation as previously described; the reactions can alternatively be carried out directly on the preformed mono- or dinucleotides.

In Formulas Ia and Ib, the substituents at Y', Z', Y, and Z generally are, but are not limited to, alcohols, ethers, esters, carbamates, carbonates, or acetals where the substituents on oxygen are generally described by Formula II and/or Formula III. The substituents can be introduced as follows:

Ethers can be readily prepared by reacting a hydroxyl group of the furanose in a nucleoside with an alkylating agent in the presence of a suitable base in an appropriate solvent.

Esters can be readily prepared by reacting a hydroxyl group of the furanose in a nucleoside or nucleotide with an activated form of an appropriate organic acid, such as an acid halide or acid anhydride in the presence of an organic or inorganic base. Alternately, a suitable coupling reagent such as dicyclohexylcarbodiimide, or 1,1'-carbonyldiimidazole can be used to activate the organic acid to achieve similar results.

Carbamates or thiocarbamates can be most conveniently prepared by reaction of a hydroxyl group of the furanose in a nucleoside or nucleotide with any of a number of commercially available isocyanates or isothiocyanates, respectively, in an inert solvent. Alternately, when a desired isocyanate or isothiocyanate is not obtainable from commercial sources, it can be prepared from the corresponding amine by the use of phosgene or thiophosgene, or a chemical equivalent, respectively.

Carbonates or thiocarbonates can be synthesized by reacting the hydroxyl group of a furanose in a nucleoside or nucleotide with an appropriate haloformate in the presence of an organic or inorganic base.

Nucleosides can be converted into nucleotide monophosphates using phosphorous oxychloride in trimethyl phosphate. Hydrolysis and workup, followed by chromatographic purification gives the corresponding monophophate derivatives. Monophosphates can be further modified to give di- or triphosphates, phosphonic anhydride derivatives, phosphonamide derivatives, dinucleotide polyphosphates, dinucleotide phosphonate/ phosphate anhydrides, or dinucleotide imidophosphate derivatives using literature procedures.

In Formulas I, Ia and Ib, the substituents at Y' and Z', and/or Y and Z, are optionally taken together to form acetals, ketals or orthoesters. Acetals and ketals can be readily prepared by reaction of adjacent 2'-and 3'-hydroxyl groups of the furanose in an appropriate nucleoside or nucleotide with an aldehyde or ketone, or their chemical equivalents, respectively, in the presence of an acid catalyst. Particularly advantageous is to use an organic acid such as formic acid, which can effect the transformation without completely affecting the integrity of the rest of the molecule. Alternately, strong acids such as trichloroacetic, p-toluenesulfonic, methanesulfonic and the like can be employed in catalytic amounts, in conjunction with inert solvents. In some cases it is preferable to use a strong acid in combination with another acid such as formic acid.

Similarly, cyclical orthoesters can be prepared by reaction of adjacent 2'-and 3'-hydroxyl groups of a furanose with an acylic orthoester in the presence of an acid.

When the nucleoside or nucleotide to be derivatized is a purine that contains a 6-amino functionality or is a pyrimidine that contains a 4-amino functionality, it can be converted to the respective urea or thiourea by treatment with isocyanates or isothiocyanates, respectively, as was previously described for carbamates or thiocarbamates of the 2'-or 3'-hydroxyls and/or 2" or 3" hydroxyls of the furanose rings. It has been found that reactions of the amino group with isocyanates or isothiocyanates can be carried out in the presence of the hydroxyl groups of the furanose, by appropriate manipulation of the stoichiometry of the reaction.

All of the derivatization reactions described can be carried out on preformed dinucleotide polyphosphates, which result in multiple products. Relative product ratios depend upon reaction stoichiometry and on whether multiple reactive groups are present. When multiple products are obtained, these can be conveniently separated by the use of preparative reverse-phase high performance liquid chromatography (HPLC). Particularly advantageous is the use of C18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Furthermore, the use of ammonium acetate buffer solutions in conjunction with methanol allows the chromatographed products to be isolated following evaporation and lyophilization of the volatile salt.

While separation of multiple products can be done by HPLC, another strategy to increase the yield of desired product from a reaction sequence is to first introduce protecting groups into nucleoside- or nucleotide-starting materials. This strategy can produce materials, which have a single reactive functionality available for reaction with a subsequent reagent. Protecting groups can be introduced on preformed dinucleotide polyphosphates, or alternately, can be carried out on nucleoside mono-, di-, or triphosphates. These materials can be purified by chromatography or other means. Further functionalization, followed by deprotection leads to a selectively-functionalized product. This new material can be used in further condenstion reactions, or can be the end product desired in the sequence.

Those having skill in the art will recognize that the starting materials can be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

Methods of Administration

The active compounds disclosed herein can be administered to the eyes of a patient by any suitable means, but are preferably administered by administering a liquid or gel suspension of the active compound in the form of drops, spray or gel. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses, which are placed on the eye. Another embodiment of the present invention involves the active compound contained within a swab or sponge, which can be applied to the ocular surface. Another embodiment of the present invention involves the active compound contained within a liquid spray, which can be applied to the ocular surface. Another embodiment of the present invention involves an injection of the active compound directly into the ocular tissues, such as subconjunctival, subscleral, or intravitrial injection, or onto the eye surface.

The quantity of the active compound included in the topical solution is an amount sufficient to achieve dissolved concentrations of the active compound on the ocular surface of the subject of from about $10^{-7}$ to about $10^{-1}$ moles/liter, and preferably from about $10^{-6}$ to about $10^{-2}$ moles/liter, and more preferably from about $10^{-4}$ to about $10^{-2}$ moles/liter in order to decrease intraocular pressure.

The topical solution containing the active compound can also contain a physiologically compatible vehicle, as those skilled in the ophthalmic art can select using conventional criteria. The vehicles can be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound would be absorbed into the bloodstream via the lungs and subsequently contact the ocular tissues in a pharmaceutically effective amount. The respirable particles can be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles which the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing active compounds are in the form of tablets, lozenges, aqueous or oily suspensions, dispersible powders or granules, emulsion, hard or soft capsules, or syrups or elixirs. Compositions intended for oral use can be prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, or liquid suspension form of a therapeutically effective amount of the active compound.

The method of the present invention can be used with other therapeutic and adjuvant agents commonly used to reduce intraocular pressure, thus enhancing the effects of therapeutic agents and adjunctive agents used to treat and manage the different types of glaucoma. Therapeutic agents used to treat narrow angle or acute congestive glaucoma include, for example, physostigmine salicylate and pilocarpine nitrate. Adjunctive therapy used in the management of narrow angle glaucoma includes, for example, the intravenous administration of a carbonic anhydrase inhibitor such as acetozolamide to reduce the secretion of aqueous humor, or of an osmotic agent such as mannitol or glycerin to induce intraocular dehydration. Therapeutic agents used to manage wide angle or chronic simple glaucoma and secondary glaucoma include, for example, prostaglandin analogs, such as Xalatan® and Lumigan®, beta-adrenergic antagonists such as timolol maleate, alpha-adrenergic agonists, such as brimonidine and apraclonidine, cholinergic agents, such as pilocarpine, and carbonic anhydrase inhibitors, such as Dorzolamide®.

High doses may be required for some therapeutic agents to achieve levels to effectuate the target response, but may often be associated with a greater frequency of dose-related adverse effects. Thus, combined use of the compounds of the present invention with agents commonly used to treat glaucoma allows the use of relatively lower doses of such agents resulting in a lower frequency of adverse side effects associated with long-term administration of such therapeutic agents. Thus, another indication of the compounds in this invention is to reduce adverse side effects of drugs used to treat glaucoma, such as the development of cataracts with long-acting anticholinesterase agents including demecarium, echothiophate, and isoflurophate.

The invention is illustrated further by the following examples that are not to be construed as limiting the invention in scope to the specific procedures described in it.

EXAMPLES

Example 1

Effects of Furanose-Modified Nucleotides on Intraocular Pressure in Rabbits The actions of 2'-(O)-, 3'-(O)-(benzyl)methylenedioxy-adenosine-5'-triphosphate (Compound 1) and 2'-(O)-, 3'-(O)-(benzyl)methylenedioxy-2"-(O)-,3"-(O)-benzyl methylenedioxy-$P^1$, $P^4$-di(adenosine 5'-)tetraphosphate (Compound 2) on intraocular pressure (IOP) were assessed in New Zealand white rabbits.

Intraocular pressure measurements: IOP was measured using a TONOPEN contact tonometer supplied by MENTOR (USA). Ten microliters of the agents were applied topically and unilaterally to the cornea, whereas the contralateral eye received the same volume of saline solution. The corneas were anesthetized to avoid any discomfort associated with the use of the tonometer. Two measurements were made before application of the agents.

Pharmacological studies: Compounds were prepared at a concentration of 0.25 mM in 0.9% saline and intraocular pressure was measured at 0.5, 1, 2, and 5 hours after the application. A single dose was tested in a single animal on a single day.

Figure 2:
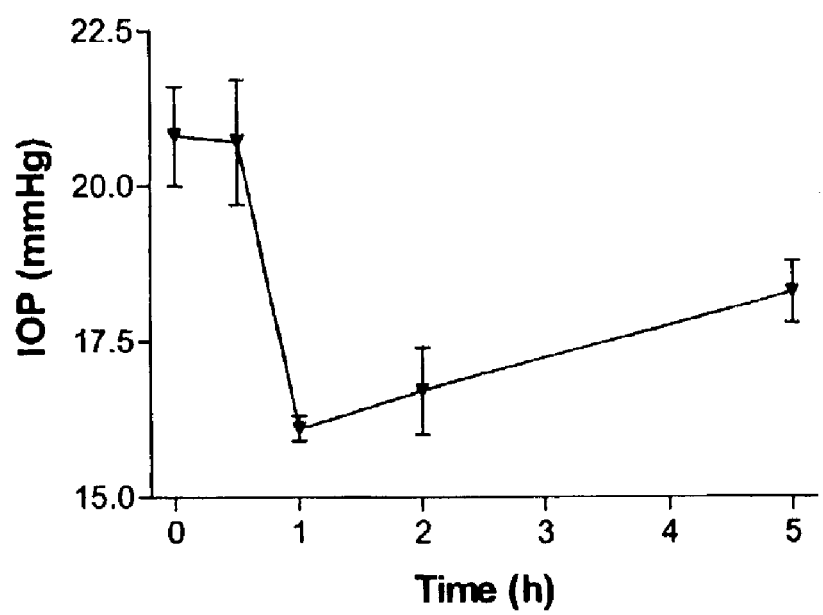
FIG. 2 shows the reduction of intraocular pressure in New Zealand white rabbits by 2'-(O)-3'-(O)-(benzyl) methylenedioxy-2"-(O)-,3 "-(O)-(benzyl)methylenedioxy-$P^1$,$P^4$-di(adenosine 5'-)tetraphosphate.

Effect of compounds 1 and 2 on rabbit IOP: Compound 1 produced a time-dependent reduction in IOP which was maximal at 1–2 hours, with a reduction of 21% (n=4) (FIG. 1). Compound 2 also produced a time-dependent reduction in IOP, which was maximal at 1 hour, with a reduction of 22% (n=4) (FIG. 2). This lowering of intraocular pressure in rabbits by compounds 1 and 2 demonstrates the utility of these compounds in treating ocular hypertension and glaucoma.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A method of reducing intraocular pressure comprising administering to a subject a pharmaceutical composition comprising an effective amount of a compound of Formula I, or a pharmaceutically-acceptable salt thereof:

Formula I wherein:

$X_1$, $X_2$, and $X_3$ are independently oxygen, methylene, monochloromethylene, dichloromethylene, monofluoromethylene, difluoromethylene, or imido;

T, W, and V are independently oxygen or sulfur;

m=0, 1 or 2;

n=0 or 1;

p=0, 1, or 2;

where the sum of m+n+p is from 0 to 5;

each M is independently hydrogen or a pharmaceutically-acceptable inorganic or organic counterion;

A=M, or

A is a nucleoside residue which is defined as:

and is linked to the phosphate chain via the 5' position of the furanose or carbocycle;

Z is H, F or $OR_1$;

Z' is H, F or $OR_3$;

Y is H, F or $OR_2$;

Y' is H, F or $OR_4$;

$R_1$, $R_2$, $R_3$, and $R_4$ are independently H or a residue according to Formulas II and/or III;

provided that when A=M, at least one of Y' and Z' equals $OQ(R_5R_6R_7)$ under the definition of Formula II; or Y' and Z' taken together form a ring as defined in Formula III;

provided that when A is a nucleoside, at least one of Y, Y', Z, or Z' equals $OQ(R_5R_6R_7)$ under the definition of Formula II; or either Y and Z taken together, and/or Y' and Z' taken together form a ring as defined in Formula III;

$D_1$ and $D_2$ are independently O or C;

Formula II wherein:

Q is a carbon atom;

$R_5$, $R_6$, and $R_7$ are independently H, F, alkyl, cycloalkyl, aralkyl, aryl, substituted aralkyl, substituted aryl, or heterocyclic moiety, or $R_5$ and $R_6$, are taken together to form a carbocyclic or heterocyclic ring of 4 to 7 members, such that the moiety defined according to Formula II when attached to the oxygen is an ether; or $R_5$ and R6 are taken together as oxygen or sulfur doubly bonded to Q, and $R_7$ is alkyl, cycloalkyl, aralkyl, substituted aralkyl, aryl, substituted aryl, or a heterocycle of 4 to 7 members, such that the moiety defined according to Formula II when attached to the oxygen is an ester or thioester; or $R_5$ and R6 are taken together as oxygen or sulfur doubly bonded to Q, and $R_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II when attached to the oxygen is a carbamate or thiocarbamate; or $R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II when attached to the. oxygen is a carbonate or thiocarbonate;

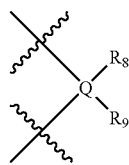

Formula III wherein $R_1$ and $R_2$ and/or $R_3$ and $R_4$ are taken together to form Q;

Q is a carbon atom;

$R_8$ and $R_9$ are taken together as oxygen or sulfur doubly bonded to Q to form a cyclical carbonate or thiocarbonate; or $R_8$ is hydrogen, alkyl, cycloalkyl, aralkyl, aryl, substituted aralkyl, or substituted aryl, heterocycle or substituted heterocycle;

$R_9$ is hydrogen, alkyl, cycloalkyl, aralkyl, aryl, substituted aralkyl, or substituted aryl, heterocycle or substituted heterocycle, alkyloxy, cycloalkyloxy, aralkyloxy, aryloxy, substituted aralkyloxy, or substituted aryloxy, such that Q is part of an acetal-, ketal- or ortho ester moiety;

B and B' are independently a purine or a pyrimidine residue according to Formulas IV or V which is linked to the sugar via the 9- or 1-position, respectively;

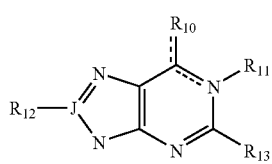

Formula IV

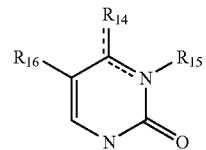

Formula V wherein:

$R_{10}$ and $R_{14}$ are independently hydroxy, oxo, amino, mercapto, alkylthio, alkyloxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or $R_{10}$ and $R_{14}$ are independently acylamino, according to Formula VI; or when $R_{10}$ or $R_{14}$ has as its first atom nitrogen, $R_{10}$ and $R_{11}$ or $R_{14}$ and $R_{15}$ are taken together to form a 5-membered fused imidazole ring, optionally substituted on the imidazole ring of the etheno-compound with a substituted- or unsubstituted-alkyl, cycloalkyl, aralkyl, or aryl moiety;

J is carbon or nitrogen, with the provision that when J is nitrogen, $R_{12}$ is not present;

$R_{11}$ is hydrogen, O or is absent;

when present, $R_{12}$ is hydrogen, alkyl, azido, amino, alkylamino, arylamino or aralkylamino, hydroxy, alkoxy, aryloxy or aralkyloxy, sulfhydryl, alkylthio, arythio or aralkylthio, or $\omega$-X($C_{1-6}$alkyl)G-, wherein X is substituted- or unsubstituted-amino, mercapto, hydroxy or carboxyl and G is chosen from —O—, —S—, —NR$_{18}$—,—N(CO)R$_{18}$—, or N(CO)OR$_{18}$;

$R_{13}$ is hydrogen, chlorine, fluorine, hydroxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;

$R_{15}$ is hydrogen, or acyl;

$R_{16}$ is hydrogen, halo, -alkyl, aryl, aralkyl, alkenyl, alkynyl, substituted or unsubstituted;

Formula VI wherein:

W is oxygen or sulfur;

$R_{17}$ is amino or mono- or disubstituted amino such that the moiety according to Formula VI is a urea or thiourea; or $R_{17}$ is alkoxy, aralkyloxy, aryloxy, substituted or unsubstituted, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide; and $R_{18}$ is alkyl, cycloalkyl, aralkyl, or aryl, with or without substituents or heteroatoms.

2. The method according to claim 1, wherein said method further comprises the step of measuring the intraocular pressure of said subject before administering the composition.

3. The method according to claim 1, further comprising the step of measuring the intraocular pressure of said subject after administering the composition.

4. The method according to claim 1, wherein administering said pharmaceutical composition to said subject is to treat ocular hypertension.

5. The method according to claim 4, wherein administering said pharmaceutical composition to said subject is to treat glaucoma.

6. The method according claim 1, wherein said pharmaceutical composition is co-administered to said subject with other therapeutic agent or adjuvant therapy commonly used to reduce intraocular pressure.

7. The method according to claim 1, wherein at least one of B or B' is an adenine.

8. The method according to claim 1, wherein said compound is a compound of Formula Ia:

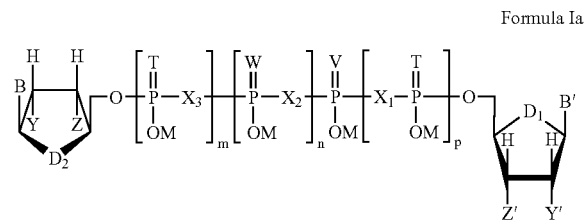

Formula Ia wherein:

M=H, or pharmaceutically-acceptable salt of this acid;

Z is H, or OR$_1$;
Z' is H, or OR$_3$;
Y is H, or OR$_2$;
Y' is H, or OR$_4$;
provided that at least one of Y, Y', Z, and Z' equals OQ(R$_5$R$_6$R$_7$) under the definition of Formula II; or Y and Z taken together, or Y' and Z' taken together form a ring as defined in Formula III;
D$_1$=O;
D$_2$=O or C;
at least one of B or B' is an adenine residue according to Formula IV; and
the sum of m+n+p is 3.

9. The method according to claim 8, wherein D=O, B=B'=adenine, R$_1$, R$_2$, R$_3$, and R$_4$ are independently H or CR$_5$R$_6$R$_7$, wherein R$_5$=R$_6$=H, and R$_7$=alkyl or arylakyl, provided at least one of Y, Y', Z, and Z' equals to OCR$_5$R$_6$R$_7$.

10. The method according to claim 9, wherein said compound is selected from the group consisting of di-5'-[(2'-O-benzyl)adenosine] tetraphosphate, di-5'-[(3'-O-benzyl)adenosine] tetraphosphate, di-5'-[(2',3'-di-O-benzyl)adenosine] tetraphosphate, di-5'-[(2'-O-phenylethyl)adenosine] tetraphosphate, di-5'-[(3'-O-phenylethyl)adenosine] tetraphosphate, and di-5'-[(2',3'-di-O-phenylethyl)adenosine] tetraphosphate.

11. The method according to claim 9, wherein said compound is selected from the group consisting of P$^1$-5'-(2'-O-benzyl)adenosine-P$^4$-5"-adenosine tetraphosphate, P$^1$-5'-(3'-O-benzyl)adenosine-P$^4$-5"-adenosine tetraphosphate, P$^1$-5'-(2'-O-benzyl)adenosine-P$^4$-5"-(3"-O-benzyl)adenosine tetraphosphate, P$^1$-5'-(2'-O-phenylethyl)adenosine-P$^4$-5"-adenosine tetraphosphate, P$^1$-5'-(3'-O-phenylethyl)adenosine-P$^4$-5"-adenosine tetraphosphate, and P$^1$-5'-(2'-O-phenylethyl)adenosine-P$^4$-5"-(3"-O-phenylethyl)adenosine tetraphosphate.

12. The method according to claim 8, wherein D=O, B=B'=adenine, R$_1$, R$_2$, R$_3$, and R$_4$ are independently H or CR$_5$R$_6$R$_7$, wherein R$_5$ and R$_6$ are taken together as oxygen, and R$_7$=alkyl or arylakyl, provided at least one of Y, Y', Z, and Z' equals to OCR$_5$R$_6$R$_7$.

13. The method according to claim 12, wherein said compound is selected from the group consisting of di-5'-[(2'-O-benzoyl)adenosine] tetraphosphate, di-5'-[(3'-O-benzoyl)adenosine ] tetraphosphate, di-5'-[(2',3'-di-O-benzoyl)adenosine] tetraphosphate, di-5'-[(2'-O-phenylacetyl)adenosine] tetraphosphate,di-5'-[(3'-O-phenylacetyl] tetraphosphate, di-5'-[(2',3'-di-O-phenylacetal)adenosine] tetraphosphate.

14. The method according to claim 12, wherein said compound is selected from the group consisting of P$^1$-5'-(2'-O-benzoyl)adenosine-P$^4$-5"-adenosine tetraphosphate, P$^1$-5'-(3'-O-benzoyl)adenosine-P$^4$-5"-adenosine tetraphosphate, P$^1$-5'-(2'-O-benzoyl)adenosine-P$^4$-5"-(3"-O-benzoyl)adenosine tetraphosphate, P$^1$-5'-(2'-O-phenylacetyl)adenosine-P$^4$-5"-adenosine tetraphosphate, P$^1$-5'-(3'-O-phenylacetal)adenosine-P$^4$-5"-adenosine tetraphosphate, and P$^1$-5'-(2'-O-phenylacetyl)adenosine-P$^4$-5"-(3"-O-phenylacetyl)adenosine tetraphosphate.

15. The method according to claim 1, wherein said compound is a compound of Formula Ib:

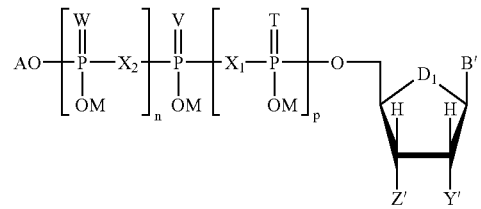

Formula Ib wherein:
A=M;
X$_1$ and X$_2$=O;
T, V, and W=O;
M=H or a pharmaceutically-acceptable salt of this acid;
Y' is H, or OR$_4$;
Z' is H, or OR$_3$;
provided at least one of Y' and Z' is OR$_3$ or OR$_4$, respectively;
with the provision that at least one of R$_3$ or R$_4$ is a residue according to Formula II;
or that Y' and Z' taken together form a ring as defined in Formula III;
D$_1$=O or C;
B' is an adenine residue according to Formula IV; and
the sum of n+p is 2.

16. The method according to claim 15, wherein D$_1$=O, B'=adenine, R$_3$=R$_4$=alkyl or arylakyl, provided at least one of Y' and Z' equals to OR$_3$ or OR$_4$.

17. The method according to claim 16, wherein said compound is selected from the group consisting of 5'-(2'-O-benzyl)adenosine triphosphate, 5'-(3'-O-benzyl)adenosine triphosphate, 5'-(2',3'-di-O-benzyl)adenosine triphosphate, 5'-(2'-O-phenylethyl)adenosine triphosphate, 5'-(3'-O-phenylethyl)adenosine triphosphate, and 5'-(2',3'-di-O-phenylethyl)adenosine triphosphate.

18. The method according to claim 15, wherein D=O, B=B'=adenine, R$_3$ and R$_4$ are independently H or CR$_5$R$_6$R$_7$, provided at least one of Y' and Z' equals to OCR$_5$R$_6$R$_7$, wherein R$_5$ and R$_6$ are taken together as oxygen, and R$_7$=alkyl or arylakyl.

19. The method according to claim 18, wherein said compound is selected from the group consisting of 5'-(2'-O-benzoyl)adenosine triphosphate, 5'-(3'-O-benzoyl)adenosine triphosphate, 5'-(2',3'-di-O-benzoyl)adenosine triphosphate, 5'-(2'-O-phenylacetyl)adenosine triphosphate, 5'-(3'-O-phenylacetyl)adenosine triphosphate, and 5'-(2',3'-di-O-phenylacetyl)adenosine triphosphate.

20. The method according to claim 1, wherein said compound is a compound of Formula Ic, or a pharmaceutically-acceptable salt thereof:

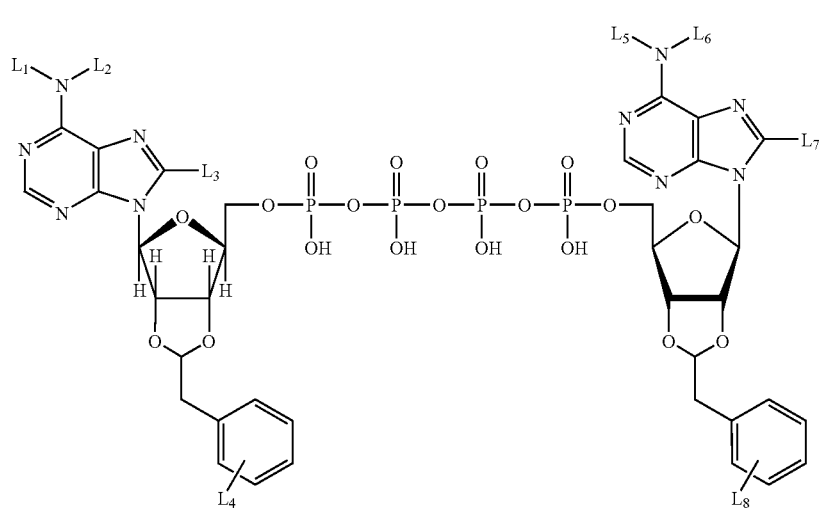

Formula Ic wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ and $L_8$ are independently selected from the group consisting of H, $C_1$–$C_6$ alkyl, aryl, $C_1$–$C_3$ alkylthio, $CF_3$, $CF_2CF_3$, —CN and —$N_3$.

21. The method according to claim 20, wherein $L_1=L_2=L_3=L_4=L_5=L_6=L_7=L_8=H$.

22. The method according to claim 1, wherein said compound is a compound of Formula Id, or a pharmaceutically-acceptable salt thereof, or a 2'-ester or ether thereof, or 3'-ester or ether thereof:

wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

23. The method according to claim 22, wherein $L_1=L_2=L_3=L_4=L_5=L_6=L_7=H$.

24. The method according to claim 1, wherein said compound is a compound of Formula Ie, or a pharmaceutically-acceptable salt thereof:

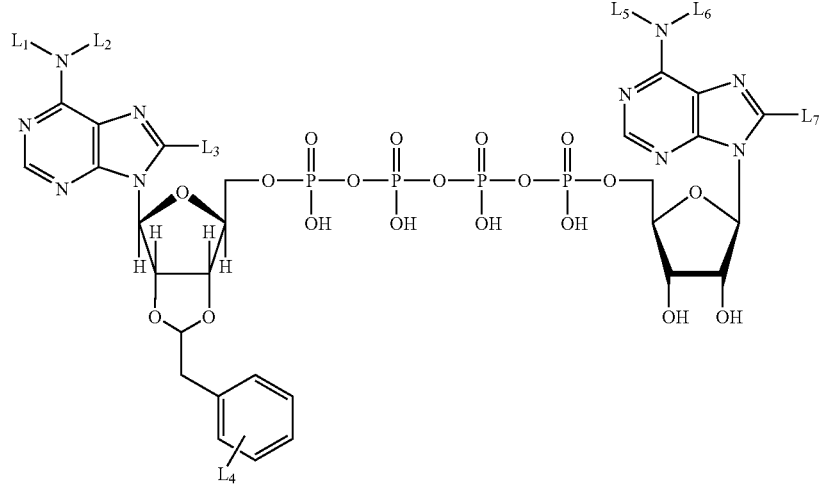

Formula Id

Formula Ie

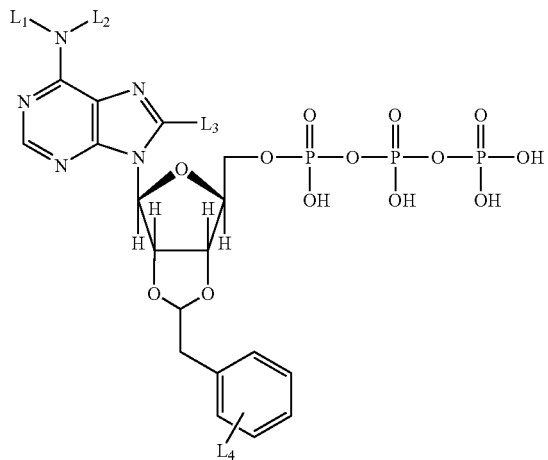

wherein $L_1$ and $L_2$ are independently selected from the group consisting of H, $C_1$–$C_4$ alkyl, phenyl, $C_1$–$C_{12}$ acyl and benzoyl;

$L_3$ is selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alklylthio, $CF_3$, $CF_2CF_3$, —CN and —$N_3$.

25. The method according to claim 24, wherein $L_1$=$L_2$=$L_3$=$L_4$=H.

26. The method according to claim 1, wherein said pharmaceutical composition is administered topically to said subject.

27. The method according to claim 1, wherein said pharmaceutical composition is administered via subconjunctival, subscleral, or intravitreal injection to said subject.

* * * * *

UNITED STATES PATENT AND TRADEMARK OFFICE
CERTIFICATE OF CORRECTION

PATENT NO. : 7,084,128 B2  Page 1 of 1
APPLICATION NO. : 10/347255
DATED : August 1, 2006
INVENTOR(S) : Benjamin R. Yerxa et al.

It is certified that error appears in the above-identified patent and that said Letters Patent is hereby corrected as shown below:

On the Title Page:

at (57), ABSTRACT, at line 4, change "purinerginic" to --purinergic--.

In the Claims:

Column 21, Claim 9, line 16, change "D=O" to --$D_2$=O--.

Column 21, Claim 12, line 41, change "D=O" to --$D_2$=O--.

Column 22, Claim 18, line 51, change "D=O" to --$D_1$=O--.

Column 22, Claim 18, line 52, change "B=B'=adenine" to --B'=adenine--.

Signed and Sealed this

Twenty-first Day of November, 2006

JON W. DUDAS
*Director of the United States Patent and Trademark Office*